United States Patent [19]

Nicolaou et al.

[11] Patent Number: 5,461,169

[45] Date of Patent: Oct. 24, 1995

[54] TOTAL SYNTHESIS OF TAXOL AND TAXOL ANALOGS

[75] Inventors: K. C. Nicolaou, La Jolla; Zhen Yang, San Diego; Jin-Jun Liu, San Diego; Hiroaki Ueno, San Diego; Philippe G. Nantermet, San Diego, all of Calif.

[73] Assignee: The Scripps Research Institute, La Jolla, Calif.

[21] Appl. No.: 197,637

[22] Filed: Feb. 16, 1994

Related U.S. Application Data

[63] Continuation-in-part of Ser. No. 193,263, Feb. 8, 1994, which is a continuation-in-part of Ser. No. 110,095, Aug. 20, 1993, Pat. No. 5,440,057, and a continuation-in-part of Ser. No. 141,847, Oct. 22, 1993, abandoned, which is a continuation-in-part of Ser. No. 64,810, May 19, 1993, abandoned, which is a division of Ser. No. 902,390, Jun. 23, 1992, Pat. No. 5,274,137.

[51] Int. Cl.$^6$ ................................................. C07D 305/14
[52] U.S. Cl. ............................................ 549/510; 549/511
[58] Field of Search ...................................... 549/510, 511

OTHER PUBLICATIONS

McMurry, J. "Carbonyl–Coupling Reactions Using Low–Valent Titanium", *Chem. Rev.*, 89: 1513–1524 (1989).

Nicolaou, et al. "Novel Chemistry of Taxol, Retrosynthetic and Synthetic Studies", *J. Chem. Soc. Chem. Comm.*, 295–296 (1994).

Chamberlin, et al. "Lithioalkanes from Arene–Sufonyl Hydrazones", *Organic Reactions*, 39: 1–83 (1990).

Ojima, et al. "New and Efficient Approches to the Semisynthesis of Taxol and its C–13 Side Chain Analogs By Means of β–Lactam Synthon Method" *Tetrahearon*, 48: 6985–7012 (1992).

Nicolaou, et al. "Synthesis of ABC Taxoid Ring Systems via a Convergent Stategy", *J. Chem. Soc. Chem. Comm.* 1024–1025 (1993).

Nicolaou, et. al. "Synthesis of a Fully Functionalized CD Ring System of Taxol", *J. Chem. Soc. Chem. Comm*, 1118–1119 (1992).

Nicolaou, et. al. "A Convergent Synthesis Toward Taxol. A Facile Enantioselective Entry Into a Fully Functionalized Ring A System", *J. Chem. Soc. Chom. Comm*, 1117–1118 (1992).

*Primary Examiner*—C. Warren Ivy
*Assistant Examiner*—Ba K. Trinh
*Attorney, Agent, or Firm*—Donald G. Lewis

[57] ABSTRACT

The total synthesis of taxol employs a convergent synthetic plan. The synthetic plan may also be employed to produce a large number of taxol analogs. Taxol analogs having skeletal extensions are inaccessible by modification of the natural product but are readily produced by employing the convergent synthetic plan herein.

1 Claim, 7 Drawing Sheets

Figure 1. Construction of C-ring, compound 7.

Figure 2. Construction of ABC ring, compound 13.

Figure 3. Total synthesis of ABCD ring system 19 and of taxol (1).

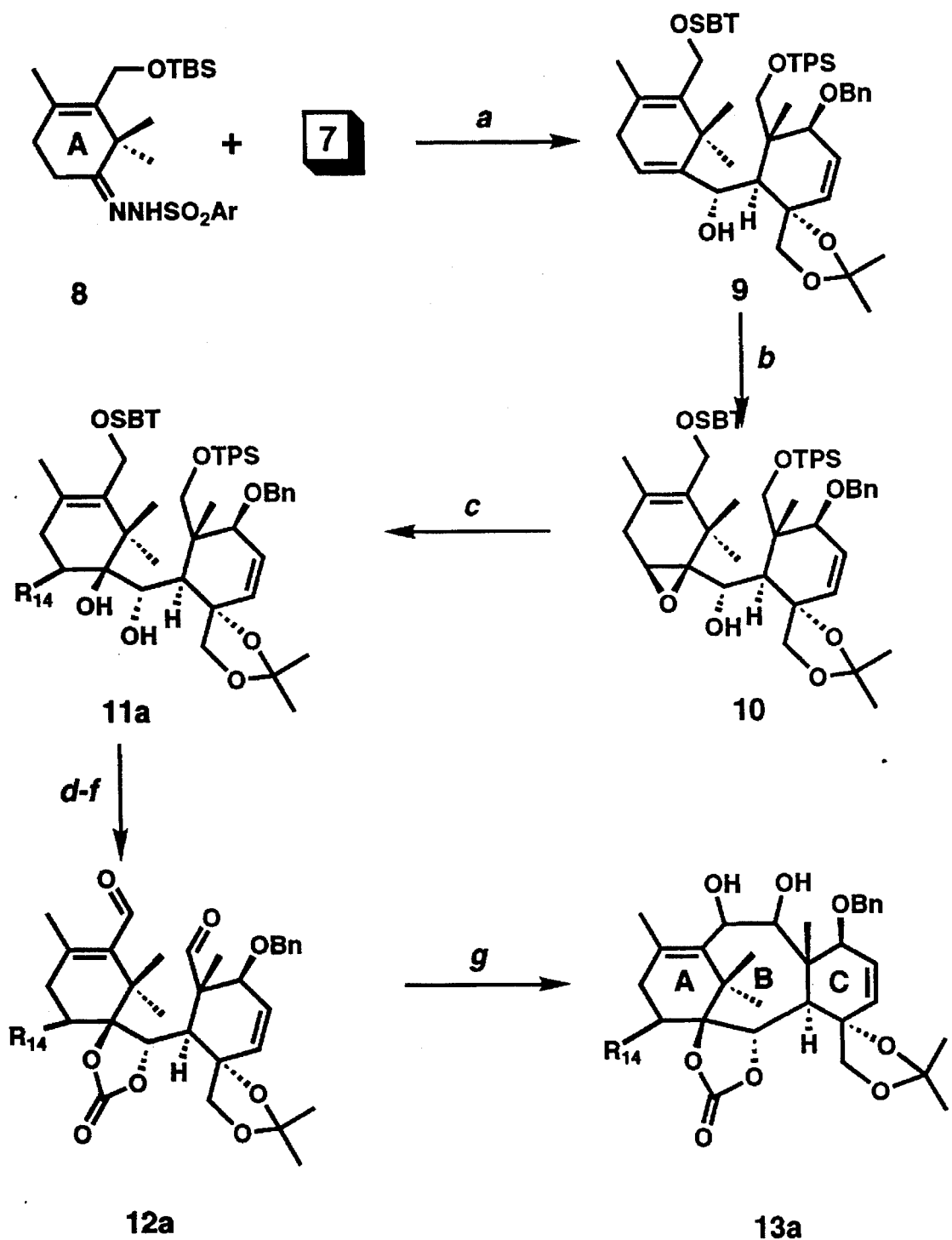
Figure 5. Adding Substituents to C-14

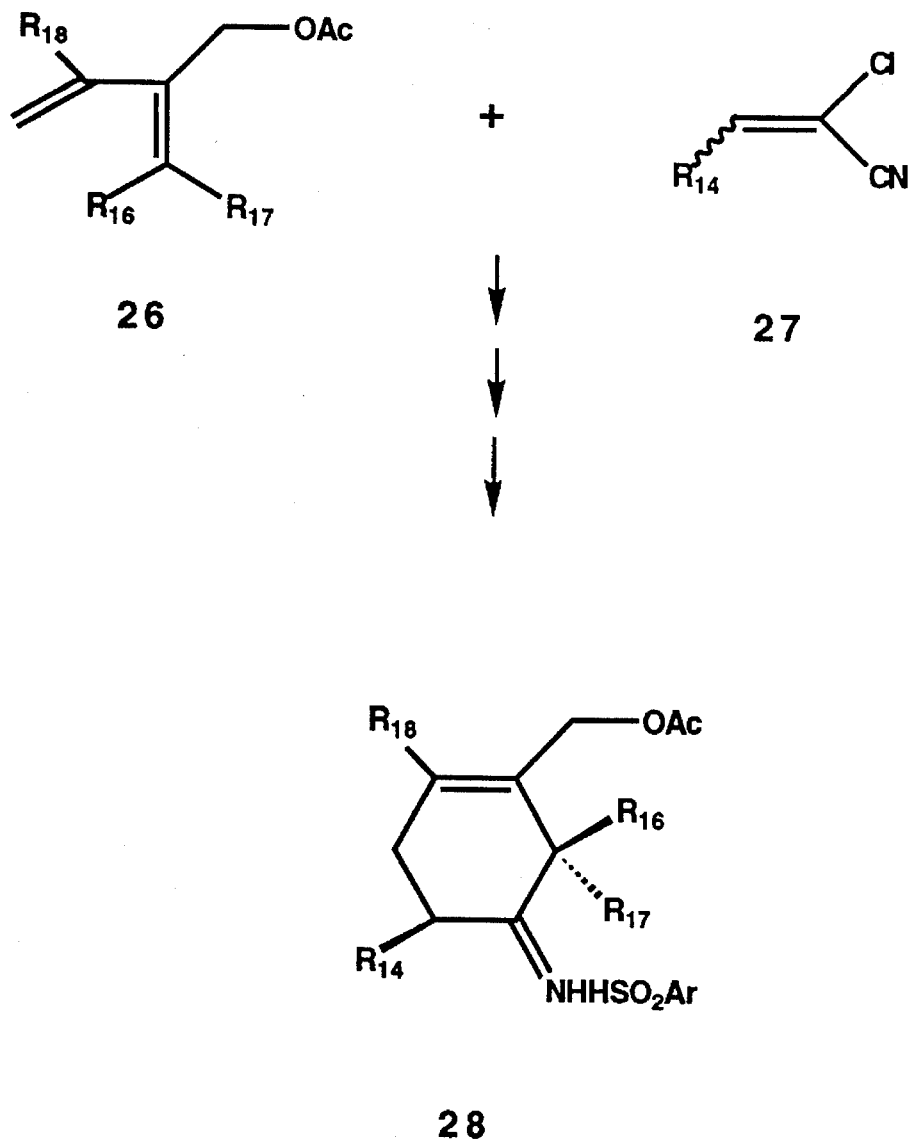
Figure 6. Incorporation of Substituents in C-14 and 16-18.

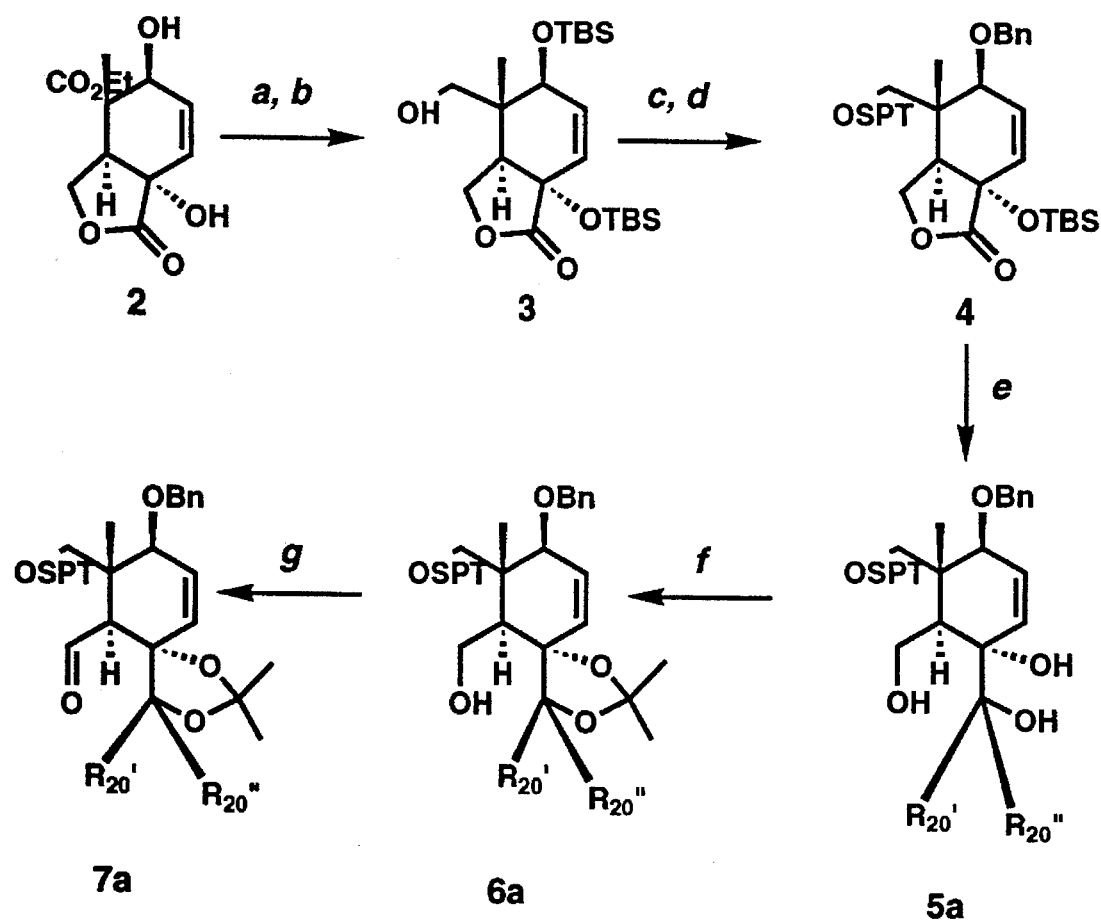
Figure 7. Adding D ring C-20 Substituents

TOTAL SYNTHESIS OF TAXOL AND TAXOL ANALOGS

GOVERNMENT RIGHTS

The invention disclosed herein was supported in part by Grant Number CA46446 from the National Institutes of Health. The United States government may have certain rights to this invention.

CROSS-REFERENCE TO RELATED APPLICATION

The present application is a continuation-in-part of U.S. patent application Ser. No. 08/193,263, filed Feb. 8, 1994, which is a continuation-in-part of U.S. patent application Ser. No. 08/110,095, filed Aug. 20, 1993 now U.S. Pat. No. 5,440,057 and is a continuation-in-part of U.S. patent application Ser. No. 08/141,847, filed Oct. 22, 1993 now abandoned, which is a continuation-in-part of U.S. patent application Ser. No. 08/064,810, filed May 19, 1993 now abandoned, which is a divisional of U.S. patent application Ser. No. 07/902,390, filed Jun. 23, 1992 now U.S. Pat. No. 5,274,137, the disclosures of which is incorporated herein by reference.

FIELD OF INVENTION

The invention relates to the total synthesis of taxol and taxol analogs. More particularly, the invention relates to the synthesis of taxol analogs having skeletal extensions.

BACKGROUND

Taxol, a substance originally isolated from the Pacific Yew tree (*Taxus brevefolia*) more than two decades ago is approved by the United States Food and Drug Adminstration for the clinical treatment of cancer patients. This molecule exerts its anticancer activity by inhibiting mitosis through enhancement of the polymerization of tubulin and consequent stabilization of microtubules. The scarcity of taxol and the ecological impact of harvesting it have prompted extensive searches for alternative sources including semisynthesis, cellular culture production and chemical synthesis. The latter has been thwarted by the magnitude of the synthetic challenge.

SUMMARY

A total synthesis of taxol is disclosed. The synthesis employs a convergent strategy, which opens a chemical pathway for the production of both the natural product itself and a variety of analogs of taxol. In particular, the method of the present invention enables the construction of modified taxol skeletons.

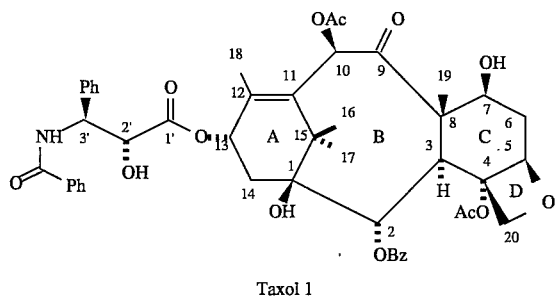

Taxol 1

The strategy for the present synthesis of taxol (1) employs the following key operations:
(1) Two fragments, representing precursors to rings A and C are coupled first by a Shapiro reaction (Chamberlin, et al., *Org. React.*, 1990, 39, pp 1–83) and then by a McMurry coupling (*Chem. Rev.*, 1989, 89, 1513–1524) to assemble an ABC ring skeleton;
(2) The D ring with its oxetane ring is then installed onto the C ring;
(3) The various substituents around the peripheries of rings B and C are added (Nicolaou, et al., *Chem. Soc., Chem. Commun.*, 1994, 295-296);
(4) The $C^{13}$ position is oxygenated; and
(5) The $C^{13}$ position is then esterified to attach the side chain (Ojima et al., *Tetrahedron* 1992, 48, pp 6985–7012).

The total synthesis of taxol outlined above also enables the total synthesis of a number of taxol analogs. Particularly important are the skeletal taxol analogs that are enabled. The present synthetic method enables the production of analogs having skeletal extensions appended to positions $C^3$, $C^7$, $C^{14}$, $C^{16}$, $C^{17}$, $C^{18}$, $C^{19}$, $C^{20'}$, and $C^{20'}$. The skeletal extensions may be alkyl or aralkyl, e.g., C1–C8 are preferred. The skeletal extensions may also include functional groups. Acetylene is a preferred functional group. However, such functional groups must be blocked and/or protected during synthesis with respect to electrophilic and nucleophilic agents and with respect to pH.

BRIEF DESCRIPTION OF THE DRAWINGS

FIG. 5 illustsrates an alternative method for appending a skeletal extension onto the $C^{14}$ position of the A ring.

FIG. 6 illustsrates further alternative methods for appending a skeletal extension onto the A ring.

FIG. 7 illustsrates methods for appending a skeletal extension onto the D ring.

DETAILED DESCRIPTION

Figure 1:
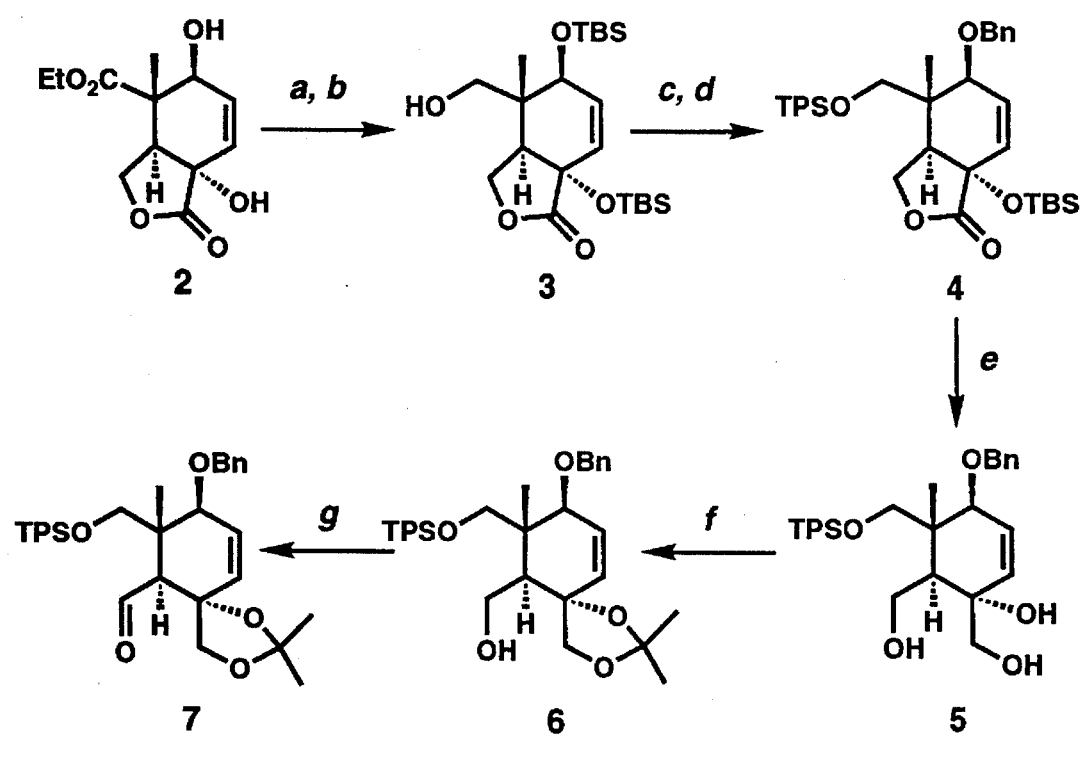
FIG. 1 schematically illustrates the construction of a preferred embodiment of an activated C ring intermediate.

The previously reported intermediates 2 (FIG. 1) (Nicolaou et al., *J. Chem. Soc., Chem. Commun.* 1992, 1118–1120) and 8 (FIG. 2) (Nicolaou, et al., *J. Chem. Soc., Chem. Commun.* 1993, 1024–1026 and *J. Chem. Soc., Chem. Commun.* 1992, 1117–1118) serve as the starting points for the convergent synthesis of taxol disclosed herein. FIG. 1 presents the construction of the requisite C-ring aldehyde 7 from 2. Protection of both hydroxyl groups in 2 with TBS groups (95%) followed by selective reduction of the ester group with LiAlH$_4$ at 0° C., furnished primary alcohol 3 (94%). Acid catalyzed deprotection of the secondary alcohol in 3 proceeded in a highly selective manner to give the corresponding diol (90% yield), which was then selectively protected with a TPS group at the primary position and a benzyl group at the secondary to afford compound 4 in 80% overall yield. The g-lactone in 4 was then reductively opened with concomitant desilylation at the tertiary position using LiAlH$_4$ at 25° C. to produce triol 5 in 80% yield. Finally, acetonide formation followed by TPAP[14] oxidation in the presence of NMO resulted in the formation of the targeted aldehyde 7 in 80% overall yield.

Figure 2:
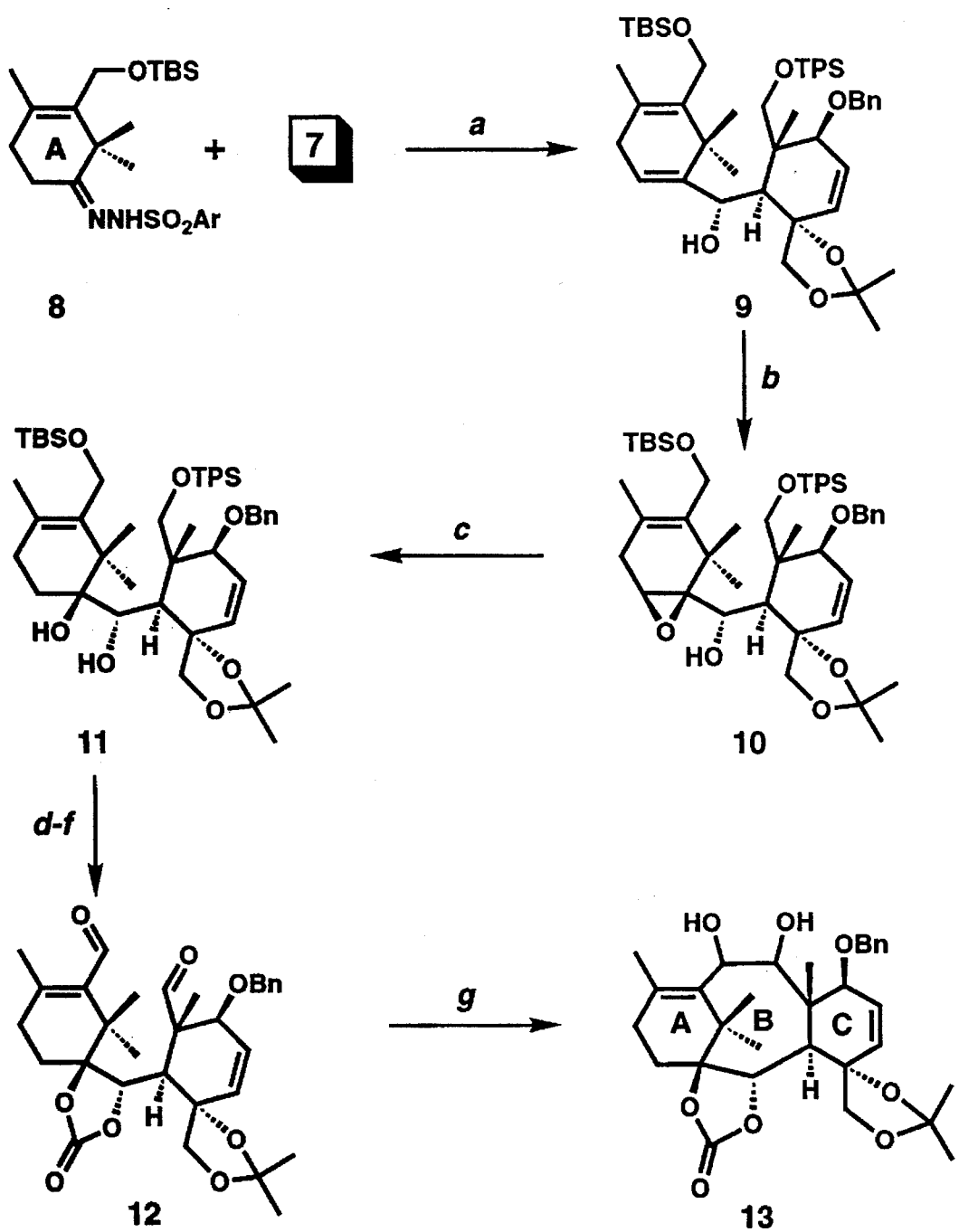
FIG. 2 schematically illustrates the joining of an A ring intermediate to a B ring intermediate to form a tricyclic ABC ring intermediate.

FIG. 2 summarizes the coupling of intermediates 7 and 8 and elaboration of the coupling product to the requisite tricyclic system 13. When the vinyl lithium reagent derived from aryl hydrazone 8 and n-C$_4$H$_9$Li was reacted with aldehyde 7 at −78° C., a single diastereoisomer of hydroxy-compound 9 was obtained in 82% yield. Directed epoxidation of the C1–C14 double bond in 9 was realized, in 87% yield, using t-C$_4$H$_9$OOH in the presence of VO(acac)$_2$ (Sharpless et al., *Aldrichimica Acta*, 1979, 12(4), 63–74) leading selectively to epoxide 10 which was regioselectively opened with LiAlH$_4$ to the 1,2-diol 11 (76% yield). X-ray crystallographic analysis of this compound (11) confirmed the designated stereochemistry for intermediates 9–11 and their relatives (FIG. 4*a*). To prepare the molecule for closure of the 8-membered B ring, and in order to create subsequent opportunities for the introduction of the benzoate functionality at C-2, diol 11 was converted to its cyclic carbonate by exposure to phosgene in the presence of KH, furnishing dialdehyde 12, after desilylation (n-(C$_4$H$_9$)$_4$NF) and oxidation (TPAP-NMO) (Griffith, et al., *Aldrichimica Acta.* 1990, 23(1), 13–19) in 32% overall yield. The suitably preorganized dialdehyde 12 was then subjected to a McMurry-type cyclization to afford the taxoid ABC ring system 13 in 23% yield (stereochemistry at the newly generated centres by X-ray crystallographic analysis of a subsequent intermediate, 13'.

Figure 3:
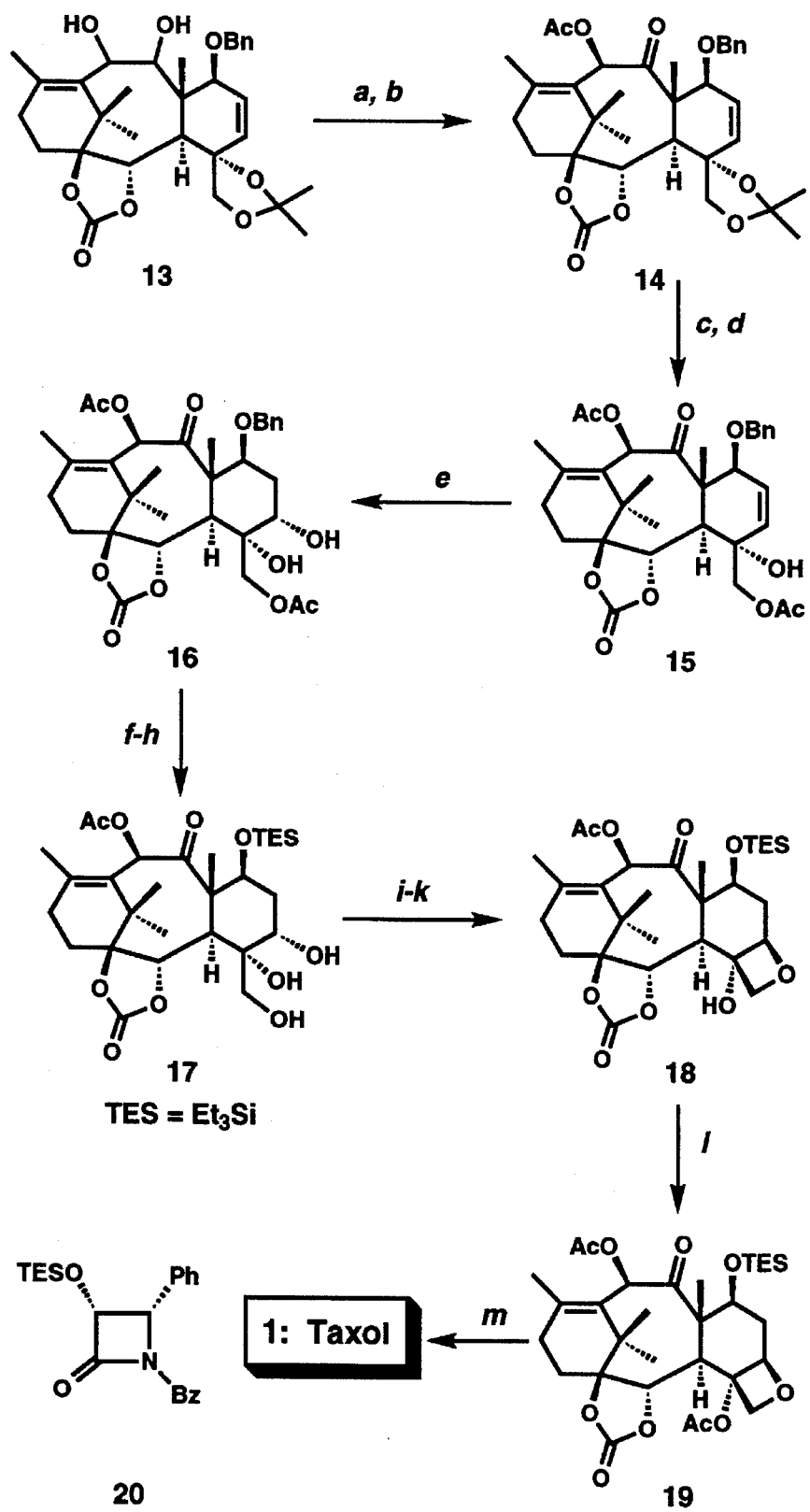
FIG. 3 schematically illustrates the installation of the D ring onto the tricyclic ABC rring intermediate followed by the esterification of the $C^{13}$ position to form taxol.

The next important intermediate in the synthesis was 19, a compound that was reached from 13 as outlined in FIG. 3. Monoacetylation of 13 followed by oxidation with TPAP-NMO furnished, regioselectively in 88% overall yield, ketoacetate 14. The stereochemistry of the acetate group at C-10 was confirmed through conversion of 14 to the crystalline benzoate 14$_{\varepsilon}$ (PCC, NaO(CO)CH$_3$, celite, benzene, D) and X-ray crystallographic analysis on the latter. Hydroboration of compound 14 followed by basic hydrogen peroxide treatment led to a mixture of two regioisomeric alcohols (55%, ca 3:1 by $^1$H NMR) which was subjected to acid induced removal of the acetonide group and chromatographic separation to afford triol 15 (35% yield from 14) as the major product. The primary hydroxyl group in 15 was then selectively acetylated under standard conditions furnishing compound 16 in 95% yield. At this stage the benzyl protecting group on the C-7 oxygen was replaced by a triethyl silyl group (TES) for reasons arising form later stages of the synthesis, and the resulting compound was selectively monodeacetylated under mildly basic conditions (K$_2$CO$_3$-CH$_3$OH) leading to triol 17 (78% overall yield). The oxetane ring was finally constructed by sequential monosilylation with TMSOTf (primary OH), triflate formation (secondary OH) and mild acid treatment to afford, after acetylation of the remaining tertiary hydroxyl group, the targeted intermediate 19 in 38% overall yield (Magee, et al., *J. Org. Chem.* 1992, 57, 3274–3276). Racemic 19, obtained from this sequence, was identical in all respects (except for optical rotation) with an authentic sample generated from taxol (1) or 10-deacetyl baccatin III (ref 17) as described elsewhere. Optically active 19 was obtained via the same route using enantiomerically pure diol 13 secured by resolution with 1(S)-(−)-camphanic chloride. Thus reaction of racemic 13 with 1(S)-(−)-camphanic chloride gave, in 86% total yield, two diastereoisomers (13' and 13") which were chromatographically separated and characterized by X-ray crystallographic analysis on one of them (more polar isomer, silica gel, 15% C$_2$H$_5$O(CO)CH$_3$ in benzene, Rf=0.21) (13", antipode to desired enantiomer). Optically pure 13 ([α]$_D^{22}$ +187° (CHCl$_3$, c 0.5)) was then generated from the correct diastereoisomer (13", less polar, silica gel, 15% C$_2$H$_5$O(CO)CH$_3$ in benzene, Rf=0.26) by exposure to methanolic K$_2$CO$_3$ (90% yield).

The conversion of compound 19 to taxol (1) followed the sequence: (i) excess C$_6$H$_5$Li, −78° C., to regioselectively open to carbonate ring and afford the desired hydroxy benzoate functionality (80%); (ii) PCC-NaO(CO)CH$_3$, benzene, reflux, to introduce a carbonyl group at C-13 (75%); (iii) excess NaB$_4$-CH$_3$OH to stereospecifically generate the C-13 hydroxyl group (83%); (iv) NaN[Si(CH$_3$)$_3$]$_2$ then Ojima's b-lactam (20), 0° C., to attach the side chain (87% yield, based on 90% conversion); and (v) HF.pyr., to remove the silyl groups (80%). Synthetic taxol was found to be identical in all respects with naturally occurring taxol, including spectroscopic characteristics ($^1$H and $^{13}$C NMR, IR, Mass spec, [α]$_D^{22}$) and biological activity (microtubule stabilization and cytotoxicity against Molt-4 leukemia cells).

The chemistry described here not only offers a solution to a formidable synthetic challenge but also opens a completely chemical avenue to taxol, other naturally occurring taxoids and synthetic, designed taxoid derivatives.

EXAMPLE I

Synthesis of Taxol

Production of a preferred activated C ring intermediate, i.e., compound 7:

A preferred embodiment of the activated C ring intermediate is illustratred as compound 7 in FIG. 1. Compound 7 can be synthesized using simple commercially available starting materials. A synthetic plan for producing compound 7 from intermediate compound 2 is illustrated in FIG. 1. In turn, compound 2 can be synthesized from simple commercially available starting materials according to the methodology illustrated in Scheme 1.

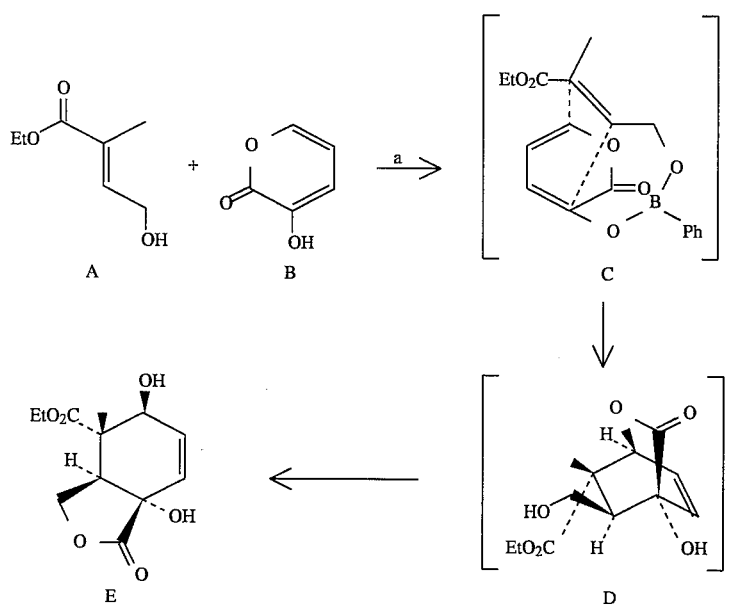

Scheme 1

Briefly, dienophile A is prepared from allyl alcohol by silylation with ʹBuMe$_2$SiCl-imidazole followed by ozonolysis, condensation with Ph$_3$-P=CH(Me)CO$_2$Et and, finally desilylation using Bu$^n$4NF (yield is 70%). As indicated in Scheme 1, product E (compound 2), is then produced intramolecularly through the action of phenylboronic acid according to the procedure reported from the Narasaka group, Narasaka, K., Simada, S., Osada, K., and Iwasawa, N. (1991), *Synthesis*, 1171. One equivalent of dienophile A is reacted with one equivalent of 3-hydroxy-2-pyrone B (Wiley, R. H., and Jarboe, C. H., (1956) *J. Am. Chem. Soc.*, 78: 2398) to give product E (compound 2) with a yield of 61%. Putative intermediates C and D have not been isloated. Product E (compound 2) may then be purified by silica gel flash chromatography, Rf=0.25 in 70% Et$_2$O/petroleum ether. Physical data for compound 2 produced according to the above protocol is disclosed by Nicolaou et al., *J. Chem. Soc., Chem. Commun.*, 1992, (Issue 16) p. 1118. The angular (tertiary) hydroxyl group of compound 2 corresponds, after many intervening synthetic steps, to the oxygenation found on the tetracyclic ABCD ring skeleton at position C$^4$. The secondary ring hydroxyl group of compound 2 corresponds, after many intervening synthetic steps, to the oxygenation found on the tetracyclic ABCD ring skeleton at position C$^7$. The oxygen of the EtO$_2$ group of compound 2 leads, after many intervening synthetic steps, to the oxygenation found on the tetracyclic ABCD ring skeleton at position C$^9$. The ring oxygen of compound 2 corresponds, after many intervening synthetic steps, to the oxygenation found on the tetracyclic ABCD ring skeleton at position C$^2$.

Compound 2 is then converted to the preferred activated C ring intermediate (compound 7) according to the synthetic plan outlined in FIG. 1.

Compound 3 is formed from compound 2 in two steps.

Step A. To a 0° C. solution of compound 2 in CH$_2$Cl$_2$, 4 equivalents of ʹBuMe$_2$SiOTf, 4 equivalents of 2,6-lutidine and 0.01 equivalents 4-dimethylaminopyridine are added; the reaction is allowed to proceed for 4 hours. The ʹBuMe$_2$Si di-ether (final yield equals 95%) is purified by silica gel flash chromatography, Rf=0.53 in 15% Et$_2$O/petroleum ether.

Step B. The ʹBuMe$_2$Si di-ether of 2 is reacted with 1.1 equivalent of LiAlH$_4$ in Et$_2$O at 0° C. for 1 hour to afford compound 3 in 94% yield. Purification of 3 is by silica gel flash chromatography, Rf=0.34 in 50% Et$_2$O/petroleum ether.

Compound 4 is formed from compound 3 in two steps.

Step C. The ʹBuPh$_2$Si ether of Compound 3 is prepared by reaction of 3 with 1.5 equivalents of ʹBuPh$_2$SiCl and 1.6 equivalents of imidazole, in DMF at 25° C. for 6 hours. The yield of the ʹBuPh$_2$Si ether is 92%. Treatment of the ʹBuPh$_2$Si ether with 0.05 equivalents of (±)-camphorsulfonic acid in MeOH/CH$_2$Cl$_2$ at 25° C., 1 hour yields (90%) the secondary allylic alcohol of 3 which is purified by silica gel flash chromatography, Rf=0.41 in 50% Et$_2$O/petroleum ether.

Step D. The secondary allylic alcohol of 3 is reacted with 1.2 equivalents of KH in Et$_2$O, in the presence of a catalytic amount of ʹBu$_4$NI, and 1.2 equivalents of PhCH$_2$Br at 25° C., for 2 hours. The yield of 4 is 87%. Compound 4 is purified by silica gel flash chromatography, Rf=0.57 in 25% Et$_2$O/petroleum ether.

Compound 5 is formed from compound 4 in one step with 80% yield.

Step E. Compound 4 is reacted with 3 equivalents of LiAlH$_4$ in Et$_2$O, at 25° C., for 12 hours. Compound 5 is purified by silica gel flash chromatography, Rf=0.23 in 50% Et$_2$O/petroleum ether.

Compound 6 is formed from compound 5 in one step with 82% yield.

Step F. Compound 5 is allowed to react with 5 equivalents of 2,2-dimethoxypropane, 0.1 equivalents of (±)-camphorsulfonic acid in CH$_2$Cl$_2$, at 25° C., for 7 hours to afford 6. Compound 6 is purified by silica gel flash chromatography, Rf=0.51 in 50% Et$_2$O/petroleum ether.

Compound 7 is formed from compound 6 in one step with 95% yield.

Step G. Compound 6 is reacted with 0.05 equivalents of tetra-n-propylammonium perruthenate, 1.5 equivalents of N-methylmorpholine-N-oxide, in $CH_3CN$, at 25° C., for 2 hour. Compound 7 is purified by silica gel flash chromatography, Rf= 0.45 in 30% $Et_2O$/petroleum ether.

Selected physical data for compound 7: $^1H$ NMR (500 MHz, $CDCl_3$, taxol numbering): d 9.98 (d, J=3.5 Hz, 1 H, 2-H), 7.65–7.12 (m, 15 H, aromatic), 5.84 (dd, J=10.5, 1.5 Hz, 1 H, 6-H), 5.71 (dd, J=10.5, 2.0 Hz, 1 H, 5-H), 4.50 (d, J=11.5 Hz, 1 H, $OCH_2Ph$), 4.22 (d, J=11.5 Hz, 1H, $OCH_2Ph$), 4.20 (d, J=9.5 Hz, 1 H, 20-H), 4.10 (dd, J=2.0, 1.5 Hz, 1 H, 7-H), 3.84 (d, J=9.5 Hz, 1 H, 20-H), 3.72 (d, J=10.0 Hz, 1 H, 9-H), 3.70 (d, J= 10.0 Hz, 1 H, 9-H), 3.18 (d, J=3.5 Hz, 1 H, 3-H), 1.42 (s, 3 H, $CH_3$-acetonide), 1.39 (s, 3 H, $CH_3$-acetonide), 1.09 (s, 9 H, $(CH_3)_3CSi$), 1.04 (s, 3 H, 19-$CH_3$); $^{13}C$ NMR (125 MHz, $CDCl_3$): d 202.3, 138.1, 135.8, 135.6, 133.0, 132.9, 131.1, 129.7, 129.7, 129.5, 128.8, 128.2, 127.6, 127.4, 127.4, 127.2, 127.2, 127.1, 108.6, 80.6, 75.4, 71.8, 70.0, 65.7, 57.6, 44.9, 26.9, 26.8, 26.5, 19.3, 13.6; IR (neat): $n_{max}$ 2931.4, 2857.0, 1720.4, 1111.5 $cm^{-1}$; HRMS (FAB): calcd for $C_{36}H_{44}O_5Si$ ($M^+$+Cs) m/z 607.2856, found 607.2865.

Production of a preferred activated A ring intermediate, i.e., compound 8:

A preferred embodiment of the activated A ring intermediate is illustrated as compound 8 in FIG. 2. A synthetic plan for producing compound 8 using simple commercially available starting materials is disclosed in detail by Nicolaou, K. C., Hwuang, C.-K., Sorensen, E. J., and Clairborne, C. F., (1992), *J. Chem. Soc. Chem. Commun.*, Issue 16: 1117. An outline of Nicolaou's synthetic plan for producing compound 8 is illustrated in Scheme 2:

Scheme 2

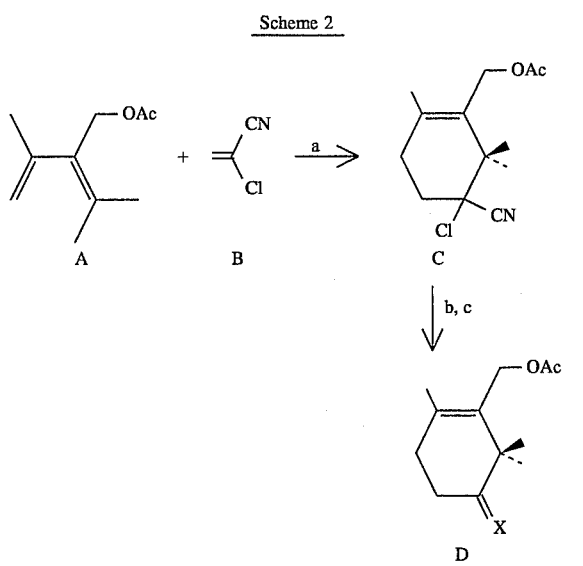

Briefly, heating of the diene A with 1.5 equivalents of 2-chloroacrylonitrile B for 96 hours at 135° C. in a sealed tube resulted in the formation of intermediate C in 85% yield. Intermediate C is purified by silica gel flash chromatography, Rf=0.25 in 10% $Et_2O$/petroleum ether. Generation of the carbonyl group from the chloronitrile C under basic conditions (5 equivalents of KOH in $^t$butanol, at 70° C. for 4 hours, afforded the corresponding hydroxyketone in 90% yield which was reacetylated under standard conditions (1.3 equivalents of $Ac_2O$, 1.3 equivalents of 4-dimethylaminopyridine in $CH_2Cl_2$ at 25° C. for 1 hour) leading to the ketoacetate D in 98% yield, where "X" represents the keto group. The ketoacetate D is converted to the hydroxy ketone under basic conditions under standard procedures and was subsequently protected as its methoxyethyl methyl ether by reacting 1.0 equivalent of the hydroxy ketone of D with 1.3 equivalents of $Pr^i_2EtN$, 1.2 equivalents of methoxyethyl methyl chloride in $CH_2Cl_2$ at 25° C. for 3 hours (yield is 95%). The methoxyethyl methyl ether of D is converted to compound 8 in a reaction with 1.0 equivalent of 2,4,6-triisopropylbenzene sulfonylhydrazide in MeOH at 25° C. for 4 hours (yield is 70%), Nicoloaou, K. C., Yang, Z., Sorensen, E. J., and Nakada, M. (1993) *J. Chem. Soc. Chem. Commun.* Issue 12: 1024. The linkage oxygen on the acetate group of diene A corresponds, after many intervening synthetic steps, to the oxygenation found on the tetracyclic ABCD ring skeleton at position $C^{10}$.

Production of a preferred bicyclic AC ring intermediate, i.e., Compound 9:

A preferred embodiment of the bicyclic AC ring intermediate is illustratred as compound 9 in FIG. 2. Compound 9 is synthesized by combining the activated A ring intermediate (compound 8) with the activated B ring intermediate (compound 8) in one step.

Step A. One equivalent of compound 8 is combined with 2.05 equivalents of $^n$BuLi in THF at −78° C. the solution is allowed warm to 25° C., and then cooled to 0° C., to which 1.0 equivalent of compound 7 in THF is added. Reaction is allowed to proceed for 0.5 hour. Compound 9 (final yield=82%) is purified by silica gel flash chromatography, Rf=0.48 in 15% $Et_2O$/petroleum ether.

Production of a preferred activated bicyclic AC ring intermediate, i.e., Compound 12:

A preferred embodiment of the activated bicyclic AC ring intermediate is illustratred as compound 12 in FIG. 2. Compound 12 is synthesized from the unactivated bicyclic AC ring intermediate (compound 9) via intermediates 10 and 11.

Compound 10 is synthesized from compound 9 in one step.

Step B. Compound 9 is allowed to react with 0.03 equivalents of $VO(acac)_2$, 3 equivalents of $^tBuOOH$ in the presence of a catalytic amount of 4-Å MS in benzene at 25° C. for 12 hours. Compound 10 (final yield=87%) is purified by silica gel flash chromatography, Rf=0.49 in 15% $Et_2O$/petroleum ether. The ring oxygen within the resultant epoxide of compound 10 corresponds, after many intervening synthetic steps, to the oxygenation found on the tetracyclic ABCD ring skeleton at position $C^1$.

Compound 11 is synthesized from compound 10 in one step.

Step C. Compound 10 is allowed to react with 3 equivalents of $LiAlH_4$ in $Et_2O$ at 25° C. for 7 hours. Compound 11 (final yield=76%) is purified by silica gel flash chromatography, Rf=0.56 in 30% $Et_2O$/petroleum ether.

Compound 12 is synthesized from compound 11 in three steps.

Step D. Compound 11 is allowed to react with 3 equivalents of KH, hexamethyl-phosphoric triamide/$Et_2O$ (30/70), $COCl_2$ (20% in benzene, 2 equivalents) at 25° C. for 2 hours. The resultant carbonate (final yield= 48%) is purified by silica gel flash chromatography, Rf=0.61 in 2% MeOH/petroleum ether.

Step E. The carbonate is allowed to react with 10 equivalents of tetra-n-butylammonium fluoride in THF at 25°

C. for 7 hours. The resultant diol (final yield=80%) is purified by silica gel flash chromatography, Rf=0.47 in 100% petroleum ether.

Step F. The diol is allowed to react with 0.05 equivalents of tetra-n-propylammonium perruthourenate, 3 equivalents of 4-methylmorpholine-n-oxide in $CH_3CN/CH_2Cl_2$ (2:1) at 25° C. for 2 hour. Compound 12, the dialdehyde (final yield= 82%), is purified by silica gel flash chromatography, Rf=0.37 in $CH_2Cl_2$/EtOAc/petroleum ether, 90/7/3.

Production of a preferred tricyclic ABC ring intermediate, i.e., Compound 13:

A preferred embodiment of the tricyclic ABC ring intermediate is illustratred as compound 13 in FIG. 2. Compound 13 is synthesized from the activated bicyclic AC ring intermediate (compound 12).

Compound 13 is synthesized from compound 12 in one step.

Step G. Compound 12 is allowed to react with 10 equivalents of $(TiCl_3)_2 \cdot (DME)_3$, 20 equivalents of Zn-Cu in DME at 70° C. for 1 hour. Compound 13 (final yield= 23%) is purified by silica gel flash chromatography, Rf=0.48 in 50% EtOAc/petroleum ether.

Selected physical data for compound 13: $^1H$ NMR (500 MHz, $CDCl_3$, taxol numbering): d 7.42–7.31 (m, 5 H, 2,4,6-triisopropylbenzene sulfonylomatic), 5.97 (dd, J=10.0, 1.5 Hz, 1 H, 5-H), 5.63 (dd, J=10.0, 1.5 Hz, 1 H, 6-H), 5.46 (d, J=5.0 Hz, 1 H, 2-H), 4.77 (d, J=12.0 Hz, 1 H, $OCH_2Ph$), 4.49 (d, J=8.5 Hz, 1 H, 20-H), 4.39 (d, J=12.0 Hz, 1 H, $OCH_2Ph$), 4.29 (d, J=5.5 Hz, 1 H, 10-H), 4.24 (d, J=5.5 Hz, 1 H, 9-H), 3.80 (d, J=8.5 Hz, 1 H, 20-H), 3.58 (b, 1 H, 7-H), 2.75–2.71 (m, 1 H, 13-H), 2.61–2.50 (m, 1 H, 13-H), 2.34 (d, J=5.0 Hz, 1 H, 3-H), 1.98–1.92 (m, 1 H, 14-H), 1.83–1.74 (m, 1 H, 14-H), 1.58 (s, 3 H, 18-$CH_3$), 1.45 (s, 3 H, 19-$CH_3$), 1.42 (s, 3 H, $CH_3$-acetonide), 1.41 (s, 3 H, $CH_3$-acetonide), 1.19 (s, 3 H, 16-$CH_3$), 1.08 (s, 3 H, 17-$CH_3$); $^{13}C$ NMR (125 MHz, $CDCl_3$): d 153.9, 139.4, 137.3, 136.1, 135.6, 128.7, 128.5, 128.3, 122.0, 108.2, 93.4, 82.4, 77.9, 75.7, 74.2, 71.2, 70.4, 69.3, 46.3, 44.3, 40.0, 31.2, 29.6, 28.9, 27.9, 26.8, 23.6, 21.7, 21.3, 16.0; IR (neat): $n_{max}$ 2970.3, 1789.1, 1455.6, 1100.3 $cm^{-1}$; HRMS (FAB) calcd for $C_{31}H_{40}O_8$ ($M^+$+Cs) m/z 673.1778, found 673.1782.

Production of a preferred activated tricyclic ABC ring intermediate, i.e., Compound 17:

A preferred embodiment of the activated tricyclic ABC ring intermediate is illustratred as compound 17 in FIG. 3. Compound 17 is synthesized from the unactivated tricyclic ABC ring intermediate (compound 13) via intermediates 14, 15, and 16.

Compound 14, FIG. 3, is prepared from compound 13 in two steps.

Step A. Compound 13 is reacted with 1.5 equivalents of $Ac_2O$, 1.5 equivalents of N-dimethylaminopyridine in $CH_2Cl_2$, at 25° C. for 2 hours. The monoacetate of 13 (final yield equals 95%) is purified by silica gel flash chromatography, Rf=0.53 in 30% EtOAc/petroleum ether.

Step B. The monoacetate is reacted with 0.1 equivalent of tetra-n-propylammonium perruthenate, 3 equivalents of 4-methylmorpholine-N-oxide in $CH_3CN$ at 25° C. for 2 hours. Compound 14 (final yield equals 93%) is purified by silica gel flash chromatography, Rf=0.55 in 30% EtOAc/petroleum ether.

Compound 15 is prepared from compound 16 in two steps.

Step C. Compound 14 is reacted with concentrated HCl in MeOH and $H_2O$ at 25° C. for 5 hours. The diol of 14 (final yield equals 80%) is purified by silica gel flash chromatography, Rf= 0.50 in 25% petroleum ether/EtOAc.

Step D. The diol is reacted with 1.5 equivalents of $Ac_2O$, 1.5 equivalents of N-dimethylaminopyridine in $CH_2Cl_2$ at 25° C. for 0.5 hour. The mono-primary acetate (final yield equals 85%) is purified by silica gel flash chromatography, Rf=0.50 in 30% petroleum ether/EtOAc.

Compound 16 is prepared from compound 15 in one step.

Step E. Compound 15 is reacted with 5.0 equivalent of $BH_3 \cdot THF$ in THF at 0° C. for 2 hours, then with $H_2O_2$, in aqueous $NaHCO_3$ for 0.5 hour. The diol, obtained with a yield of 55%, (ca. 3:1 mixture of C6–C7 regioisomers by $^1H$ NMR) is purified by silica gel flash chromatography, Rf=0.45 in 10% ether/$CH_2Cl_2$. The resultant free hydroxyl of compound 16 corresponds, after many intervening synthetic steps, to the oxygenation found in the oxime D ring of the tetracyclic ABCD ring skeleton between $C^5$ and $C^{20}$.

Compound 17 is prepared from compound 16 in three steps.

Step F. The C-4, C-5 diol, compound 16, is reacted with $H_2$ over 10% $Pd(OH)_2(C)$ in EtOAc at 25° C. for 0.5 hour, 95%; The C-7 secondary alcohol (final yield equals 95%) is purified by silica gel flash chromatography, Rf=0.45 in EtOAc.

Step G. The C-7 secondary alcohol is reacted with 25 equivalents of $Et_3SiCl$ in pyridine at 25° C. for 12 hour. The C-7 trimethylsilyl ether (final yield equals 85%) is purified by silica gel flash chromatography, Rf=0.44 in 50% EtOAc/petroleum ether.

Step H. The C-7 trimethylsilyl ether is reacted with 10 equivalents of $K_2CO_3$ in MeOH at 0° C. for 15 minutes. Compound 17 (final yield equals 95%) is purified by silica gel flash chromatography, Rf=0.35 in 50% EtOAc/petroleum ether.

Production of a preferred tretracyclic ABCD ring skeleton, i.e., Compound 18:

A preferred embodiment of the tretracyclic ABCD ring skeleton is illustratred as compound 18 in FIG. 3. Compound 18 is synthesized from the activated tricyclic ABC ring intermediate (compound 17).

Compound 18 is prepared from compound 17 in three steps.

Step I. Compound 17 is reacted with 10 equivalents of $Me_3SiCl$, 30 equivalents of pyridine in $CH_2Cl_2$ at 0° C. for 15 minutes. The primary trimethylsilyl ether (final yield equals 96%) is left as a crude mixture; product Rf=0.75 in 34% EtOAc/petroleum ether.

Step J. The mixture containing the primary trimethylsilyl ether is reacted with 15 equivalents of $Tf_2O$, 30 equivalents of $^iPr_2NEt$ in $CH_2Cl_2$ at 25° C. for 0.5 hour. The C-5 secondary triflate (final yield equals 70%) is left as a crude mixture; product Rf=0.70 in 34% EtOAc/petroleum ether.

Step K. The C-5 secondary triflate is reacted with a catalytic amount(±)-camphorsulfonic acid in MeOH at 25° C. for 10 minutes then with silica gel in $CH_2Cl_2$ at 25° C. for 4 hours. Compound 18 (final yield equals 60%, based upon 50% conversion) is purified by silica gel flash chromatography, Rf=0.36 in 34% EtOAc/petroleum ether.

Production of a preferred tretracyclic ABCD ring skeleton having an oxygenated $C^{13}$, i.e., Compound 1:

A preferred embodiment of the tretracyclic ABCD ring skeleton with an appended $C^{13}$ ester is illustrated as compound 1, i.e., taxol. Taxol (compound 1) is synthesized from the tretracyclic ABCD ring intermediate (compound 18) via intermediate 19.

Compound 19 is prepared from compound 18 in one step.

Step L. Compound 18 is reacted with 10 equivalents of $Ac_2O$, 20 equivalents of N-dimethylaminopyridine in $CH_2Cl_2$ at 25° C. for 4 hours. Compound 19 (final yield equals 94%) is purified by silica gel flash chromatography, Rf=0.70 in 40% EtOAc/petroleum ether.

Compound 20 is prepared as previously described in Farina, V,. Hauck, S. I., and Walker, D. G., (1992) *Synlett.*, 761.

Compound 1 is then formed from compound 19 and compound 20 in 5 steps.

Step M.

(i) Compound 19 is reacted with 5 equivalents of Phenyl-Li in THF at −78° C. for 10 minutes. The C-2 benzoate ester of 19 (final yield equals 80%) is purified by silica gel flash chromatography, Rf=0.57 in 50% EtOAc/petroleum ether.

(ii) The $C^2$ benzoate ester of 19 is oxygenated at the $C^{13}$ position by reaction with 30 equivalents of PCC, NaOAc, celite in benzene under reflux for 1 hour. The resulting $C^{13}$ ketone (final yield equals 75%) is purified by silica gel flash chromatography, Rf=0.57 in 50% EtOAc/petroleum ether.

(iii) The $C^{13}$ ketone is reacted with 10 equivalents of $NaBH_4$ in MeOH at 25° C. for 5 hour. The $C^{13}$ allylic alcohol (final yield equals 83%) is purified by silica gel flash chromatography, Rf= 0.32 in 50% EtOAc/petroleum ether.

(iv) The $C^{13}$ allylic alcohol is reacted with 3.5 equivalents of $NaN(SiMe_3)_2$ in THF at 0° C., then at 20° C. The $C^7$, $C^{2'}$ triethylsilyl ether of taxol (final yield equals 87% based upon 90% conversion) is purified by silica gel flash chromatography, Rf=0.59 in 50% EtOAc/petroleum ether.

(v) The $C^7$, $C^{2'}$ triethylsilyl ether of taxol is then reacted with HF•pyridine in THF at 25° C. for 1.5 hours to produce taxol (compound 1). The resultant taxol (final yield equals 80%) is purified by silica gel flash chromatography, Rf=0.12 in 50% EtOAc/petroleum ether.

Selected physical data for compound 19: $^1$H NMR (500 MHz, $CDCl_3$, taxol numbering): d 6.40 (s, 1 H, 10-H), 4.95 (d, J=9.0 Hz, 1 H, 5-H), 4.60 (d, J=9.0 Hz, 1 H, 20a-H), 4.47 (d, J=9.0 Hz, 1 H, 20b-H), 4.43 (dd, J=10.0, 7.5 Hz, 1 H, 7-H), 4.39 (d, J= 5.5 Hz, 1 H, 2-H), 3.36 (d, J=5.5 Hz, 1 H, 3-H), 2.71 (m, 1 H, 13a-H, 2.56 (m, 1 H, 6b-H), 2.17 (s, 3 H, OAc), 2.15 (s, 3 H, OAc), 2.12 (m, 1 H, $CH_2$), 2.07 (s, 3 H, 18-$CH_3$), 1.97 (m, 1 H, $CH_2$), 1.88 (m, 2 H, $CH_2$), 1.78 (s, 3 H, 19-$CH_3$), 1.23 (s, 3 H, 16-$CH_3$), 1.17 (s, 3 H, 17-$CH_3$), 0.88 (t, J=7.5 Hz, 9 H, Si($CH_2CH_3$)$_3$, 0.55 (dq, J=8.0, 3.0 Hz, 6 H, Si($CH_2CH_3$)$_3$; $^{13}$C NMR (125 MHz, $CDCl_3$); d 202.6, 170.3. 169.2, 153.1, 144.0, 130.7, 92.8, 84.0, 80.3, 80.0, 76.4, 76.1, 60.3, 43.5, 38.0, 29.7, 29.4, 25.5, 23.1, 21.9, 21.1, 19.1, 9.8, 6.7, 5.2; IR (neat) $n_{max}$ 2924, 1814, 1728, 1461, 1372, 1238, cm$^{-1}$; HRMS (FAB) calcd for $C_{31}H_{46}O_{10}Si$ (M$^+$+Cs) m/z 739.1915, found 739.1929.

EXAMPLE II

Synthesis of Taxol Analogs with Skeletal Extensions

Figure 4:
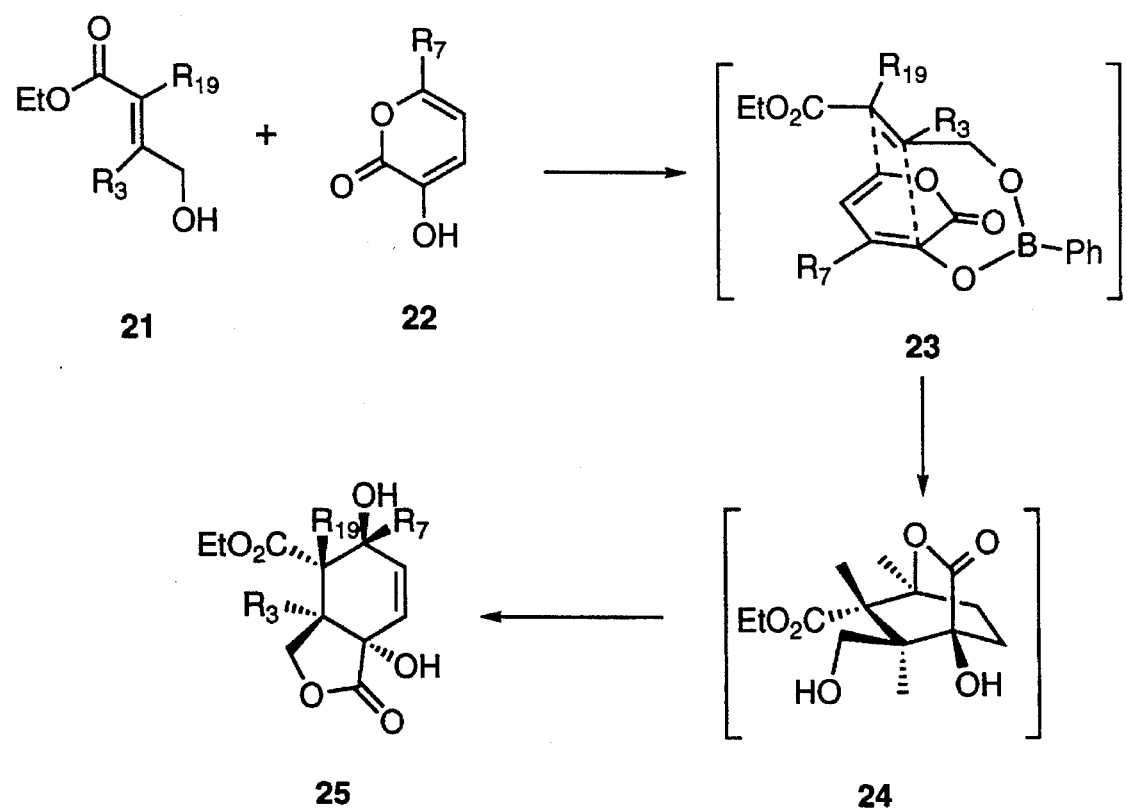
FIG. 4 schematically illustrates alternative starting materials to build a C ring intermediate with appended skeletal extensions that can be incorporated into a taxol analog.

Production of preferred Taxol Analogs with Appended Skeletal Extensions on the C Ring:

The synthesis of taxol analogs having a tetracyclic ABCD ring skeleton with appended skeletal extensions at positions $C^3$, $C^7$, and $C^{19}$ can be carried out with modified compound 2. FIG. 4 illustrates the synthesis of a preferred modification of compound 2, i.e., compound 25. Briefly, dienophile 21 is reacted with an equivalent of substituted 3-hydroxy-2-pyrone 22 to yield compound 25. The modified C ring is then carried through the remaining reactions to yield the corresponding substituted taxol.

B] Synthesis of Taxol with Sustituents at the C-14 Position.

Compound 11a is synthesized in one step (FIG. 5).

Step C. Deuteration or tritiation of compound 10 is accomplished by reacting 10 with 3 equivalents of $LiAl_2H_4$ or $LiAl^3H$ in $Et_2O$. Addition of carbon substituents to C-14 is accomplished by reacting excess RLi, $R_2CuLi$, or RMgBr, under standard conditions, with compound 10. The modified A-C ring is then carried through the remaining reactions to yield the corresponding C-14 substituted taxol.

C] Synthesis of Taxol with Sustituents on the A ring.

The synthesis of taxol A ring-analogs derivatized in their carbon skeleton at carbons 14, 16, 17 and, 18 (compound 1) is carried out with modified compound S. Synthesis of compound 28 (FIG. 6) follows that of compound S, Nicolaou, K. C., Hwuang, C.-K., Sorensen, E. J., and Clairborne, C. F., (1992), *J. Chem. Soc. Chem. Commun.*, Issue 16: 1117. FIG. 6, the diene 26 is reacted with the 2-chloroacrylonitrile, 27, followed by generation of the carbonyl group from the chloronitrile under basic conditions to afford the corresponding hydroxyketone. The hydroxyketone is reacetylated leading to the ketoacetate, which is converted to the hydroxy ketone, and subsequently protected as its methoxyethyl methyl ether (by reacting the hydroxy ketone with methoxyethyl methyl chloride. The methoxyethyl methyl ether is converted to compound 28 in a reaction with 2,4,6-triisopropylbenzenesulfonylhydrazide. Compound 28 is then carried through the remaining reactions (exemplified in FIG. 2) to yield the corresponding substituted taxol.

D] Synthesis of the taxol D-ring with substituents added to the C-20 position:

Compound 5a is formed in one step, FIG. 7.

Step E. Deuteration or tritiation of compound 4 is accomplished by reacting 4 with 3 equivalents of $LiAl^2H_4$ or $LiAl^3H_4$ in $Et_2O$ Addition of carbon substituents to C-20 is accomplished by reacting excess RLi, $R_2CuLi$, or RMgBr, under standard conditions, with compound 4. Compound 5a is then carried through the remaining reactions (exemplified in FIG. 1) to yield the corresponding C-20 substituted taxol.

We claim:

1. A process for synthesizing taxol comprising the following steps:

Step A: providing an activated A ring intermediate represented by the following structure:

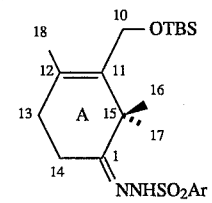

Step B: providing an activated C ring intermediate represented by the following structure:

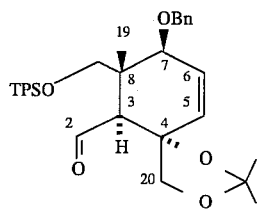

Step C: producing a bicyclic AC ring intermediate by attaching the activated $C^1$ of the activated A ring intermediate of said Step A to the activated $C^2$ of the activated C ring intermediate of said Step B, the bicyclic AC ring intermediate being represented by the following structure:

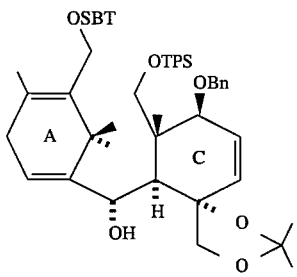

then;

Step D: activating the bicyclic AC ring intermediate of said Step C for producing an activated bicyclic AC ring intermediate having an activated $C^9$ and an activated $C^{10}$, the activated bicyclic AC ring intermediate being represented by the following structure:

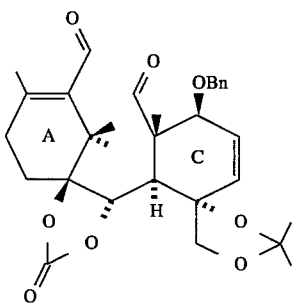

then;

Step E: producing a tricyclic ABC ring intermediate by annulating the activated bicyclic AC ring intermediate of said Step D by bonding the activated $C^9$ to the activated $C^{10}$, the tricyclic ABC ring intermediate being represented by the following structure:

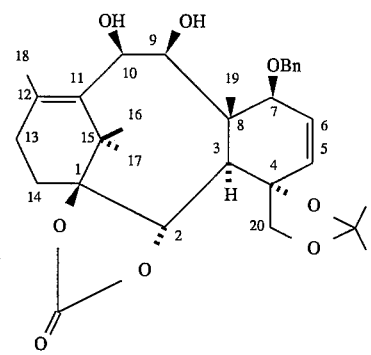

then;

Step F: activating the tricyclic ABC ring intermediate of said Step E for producing an activated tricyclic ABC ring intermediate having an activated $C^5$ and an activated $^{20}$, the activated tricyclic ABC ring intermediate being represented by the following structure:

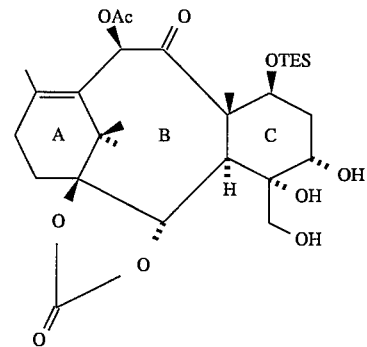

and then;

Step G: producing taxol by forming an oxygen linkage between the activated $C^5$ and the activated $C^{20}$ of the activated tricyclic ABC ring intermediate of said Step F, taxol being represented by the following structure:

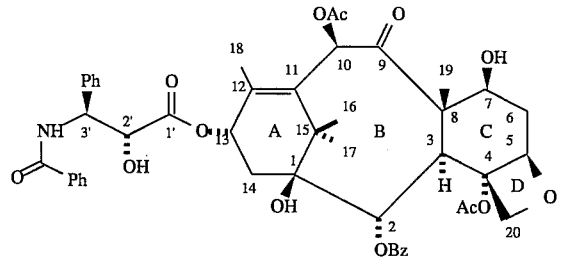

* * * * *